US00PP13032P2

(12) United States Plant Patent
Pieters

(10) Patent No.: US PP13,032 P2
(45) Date of Patent: Oct. 1, 2002

(54) CHRYSANTHEMUM PLANT NAMED 'ROME'

(76) Inventor: Dirk Pieters, Schierveldestraat 3A, Oosnieuwkerke, 8840 Staden (BE)

( * ) Notice: Subject to any disclaimer, the term of this patent is extended or adjusted under 35 U.S.C. 154(b) by 0 days.

(21) Appl. No.: 09/550,154

(22) Filed: Apr. 17, 2000

(51) Int. Cl.[7] ..... A01H 5/00
(52) U.S. Cl. ..... Plt./294
(58) Field of Search ..... Plt./294

(56) References Cited

U.S. PATENT DOCUMENTS

PP5,934 P * 4/1987 Shoesmith ..... Plt./294
PP7,516 P * 5/1991 VandenBerg ..... Plt./294
PP9,379 P * 11/1995 VandenBerg ..... Plt./294

* cited by examiner

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new plant variety of chrysanthemum producing flowers with white ray florets and yellow disc florets.

1 Drawing Sheet

BACKGROUND OF THE INVENTION

The present invention is directed to a new and distinct variety of chrysanthemum morifolium. The varietal denomination of the new chrysanthemum is 'ROME'.

The new variety is a cross of two unnamed, undistributed, unpatented seedlings. The new variety has been asexually reproduced by vegetative cuttings in Ventura County, Calif. and the distinguishing characteristics are retained through successive generations of asexual reproduction.

SUMMARY OF THE INVENTION

'ROME' is a chrysanthemum plant that produces flowers with white ray florets and yellow disc florets.

COMPARISON WITH OTHER VARIETY

The following is a comparison to the commercial variety 'GEDI WT8' (U.S. Plant Pat. No. 11,648), 'Pidoul,' Seed Parent, Pollen:

| | 'GEDI WT8' | 'ROME' | 'Pidoul' | Seed Parent | Pollen Parent |
|---|---|---|---|---|---|
| Inflorescence Diameter | 4.5 cm | 2.5 cm | 2.5 to 3 cm | 3 cm | 2 cm |
| Ray Floret coloration when mature | Near 158D | Near 155D | Near 155D | Near 155D | Yellow |
| Quantity of Ray florets | About 30 | Between 30 to 40 | About 30 | About 20 | About 70 |
| Quantity of Inflorescence per stem | About 12 | About 15 | Between 12 to 15 | About 20 | About 25 |
| Height | About 18 cm | About 21 cm | Between 25 to 30 cm | About 20 cm | About 26 cm |
| Natural Season Bloom | Early October | Early September | Mid-September | Mid-September | Early October |
| Inflorescence form | Daisy | Anemone | Daisy | Daisy | Daisy |

BRIEF DESCRIPTION OF ILLUSTRATIONS

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. Plants described are approximately 90 days old from a rooted cutting. 'ROME' has not been observed under all possible environmental conditions. The phenotype may vary with variations in the environment such as temperature, light intensity, day length and cultural conditions. The color designations herein are from *The Royal Horticultural Society Colour Chart* except where general terms are used.

To produce a commercial product the plants may be pinched once about ten days after planting. No growth retardant has been applied in the specimens described. Useful growing conditions include average night temperatures of about 17° C. to 20° C. and average day temperatures of about 20° C. to 30° C. No susceptibility or resistance to disease has been observed. Resistance or susceptibility to insects has not been observed. Seed production has not been observed. Winter hardiness and drought/heat tolerance have not been observed.

ROOTING CHARACTERISTICS

Time to initiate roots: About 7 to 14 days at about 21° C.
Rooting description: Fine, fibrous.

PLANT

Plant type: Herbaceous perennial.
Growth habit: Mounding.
Size: Height about 21 cm, width about 22 cm.
Growth rate: Rapid.
Branching characteristics: Free branching, lateral branches are approximately 18 cm in length, about 0.5 cm in diameter and near 137C in color.
Typical size containers: 4 inch, 6 inch, 2 gallon.

FOLIAGE

Arrangement: Alternate.
Compound or simple: Simple.
Quantity of leaves: Many.
Leaf size:
*Length.*—About 5.5 cm.
*Width.*—About 4 cm.
Leaf shape: Ovate.
Leaf tip: Acuminate.
Leaf base: Attenuate.
Leaf attachment: Stalked.
Petiole: Length about 2 cm, diameter about 0.3 cm, color near 137C.
Margin type: Serrate.
Texture: Lightly pubescent.
Color:
*Young foliage upper side.*—Near 137A.
*Young foliage under side.*—Near 137A.
*Mature foliage upper side.*—Near 137A.
*Mature foliage under side.*—Near 137A.
Venation: Net.
*Color.*—Venation upper side: Near 137C. Venation under side: Near 137D.

BLOOM

Inflorescence:
*Flowering habit.*—Induced by darkness period greater than 13.5 hours. Approximately 50 days of day length required to induce and develop blooms.
*Inflorescence form.*—Anemone.
*Natural flowering season.*—Around the first week in September in Ventura County, Calif.
*Quantity of inflorescences per stem.*—About 15.
*Inflorescence diameter.*—About 2.5 cm, the angle of attachment causes the overall diameter of the inflorescence to be less than the sum of the disc and ray florets measured individually. Additionally, the disc opens at an angle, causing it to partially cover the base of the ray florets as it expands, which also causes the ray floret length to appear less in the overall measurement of the entire intact inflorescence.
*Inflorescence depth.*—About 1.5 cm.
*Disc diameter.*—About 1.5 cm.
*Inflorescence longevity on plant.*—About 20 to 26 days.
*Persistence.*—Persistent.
Ray florets:
*Appearance.*—Matte.
*Texture.*—Smooth.
*Number.*—About 30–40.
*Shape.*—Obovate.
*Margin.*—Entire.
*Tip.*—Obtuse.
*Length.*—About 1.5 cm.
*Width.*—About 0.8 cm.
*Color.*—Upper side: First opening: Near 9D. Mature: Near 155D. Fading: Near 155D. Under side: First opening: Near 13D. Mature: Near 155D. Fading: Near 155D.
Disc florets:
*Appearance.*—Shiny.
*Texture.*—Smooth.
*Number.*—Over 100.
*Shape.*—Cylindric.
*Tip.*—Serrate.
*Length.*—About 0.8 cm.
*Width.*—About 0.1 cm.
*Color.*—First opening: Near 13A. Mature: Near 13A. Fading: Near 13B.
Peduncle: About 0.2 cm in diameter.
*Length.*—Terminal, shortest: About 3 cm. Lateral, longest: About 5 cm.
*Color.*—Near 138A.
*Strength.*—Soft.
*Habit.*—Erect.
Inflorescence bud:
*Length.*—About 0.8 cm.
*Diameter.*—About 0.8 cm.
*Form or shape.*—Globular.
*Color.*—Near 13A.
Involucral bracts: Length about 0.6 cm, width about 0.4 cm.
*Appearance.*—Matte.
*Texture.*—Lightly pubescent.
*Number.*—About 20 to 30.
*Shape.*—Ovate.
*Margin.*—Entire.
*Tip.*—Acute.
*Color.*—Upper side: Near 137A. Under side: Near 137A.

REPRODUCTIVE ORGANS

Ray florets:
*Pistillate.*—Pistil length in the ray florets is about 0.6 cm.
*Pistil number.*—1 per flower.
*Stigma shape.*—2 branched.
*Stigma color.*—Near 7D.
*Style length.*—About 0.3 cm.
*Style color.*—Near 7D.
Disc florets: Pistil length in the disc florets is about 0.3 cm.
*Pistillate.*—Pistil number: 1 per flower.
*Stigma shape.*—Cylindric.
*Style length.*—About 0.3 cm.
Staminate:
*Stamen number.*—About 5.
*Anther shape.*—Tubular.
*Anther color.*—Near 7A.
*Pollen color.*—Near 13A.

What is claimed is:

1. A new and distinct chrysanthemum plant of the variety substantially as herein shown and described.

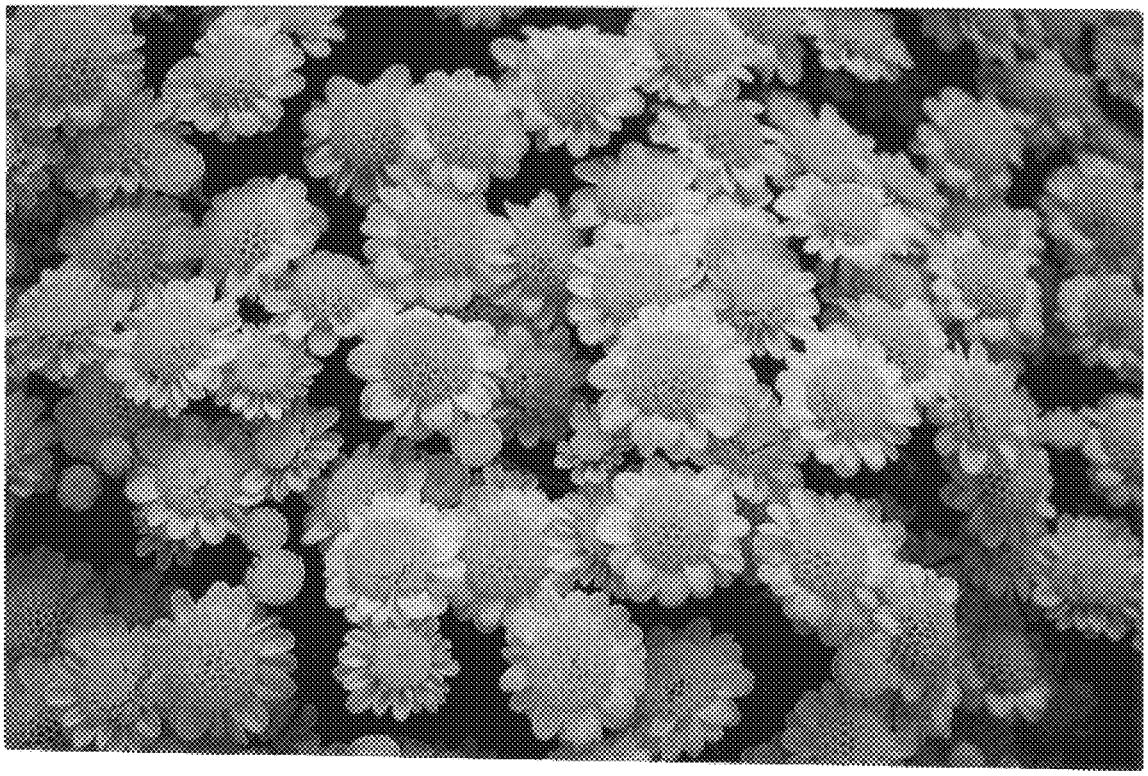

* * * * *